(12) United States Patent
Hua et al.

(10) Patent No.: US 8,702,924 B2
(45) Date of Patent: Apr. 22, 2014

(54) ELECTRODE FOR AN ELECTROCHEMICAL DEVICE AND METHOD FOR DETECTING HYDROGEN PEROXIDE USING THE ELECTRODE

(75) Inventors: Mu-Yi Hua, Taoyuan County (TW); Hsiao-Chien Chen, Taichung (TW); Rung-Ywan Tsai, Hsinchu County (TW); Kong-Wei Cheng, Hsinchu (TW)

(73) Assignee: Chang Gung University, Tao-Yuan (TW)

( * ) Notice: Subject to any disclaimer, the term of this patent is extended or adjusted under 35 U.S.C. 154(b) by 114 days.

(21) Appl. No.: 13/105,304

(22) Filed: May 11, 2011

(65) Prior Publication Data

US 2012/0031774 A1  Feb. 9, 2012

(30) Foreign Application Priority Data

Aug. 4, 2010  (TW) ............................... 99125888 A
Aug. 4, 2010  (TW) ............................... 99125889 A
Aug. 20, 2010 (TW) ............................... 99127939 A

(51) Int. Cl.
*G01N 33/487* (2006.01)

(52) U.S. Cl.
USPC ............................. 204/403.01; 204/403.02

(58) Field of Classification Search
USPC ...................................... 204/403.01–403.15
See application file for complete search history.

(56) References Cited

U.S. PATENT DOCUMENTS

| | | | |
|---|---|---|---|
| 4,814,400 A * | 3/1989 | Sansone ....................... | 525/435 |
| 2004/0038101 A1* | 2/2004 | Tanaka ........................ | 429/30 |
| 2006/0105217 A1* | 5/2006 | Fujibayashi .................. | 429/33 |
| 2007/0128491 A1* | 6/2007 | Chisholm et al. ............ | 429/33 |
| 2011/0081591 A1* | 4/2011 | Scherer et al. ............... | 429/457 |
| 2011/0262835 A1* | 10/2011 | Unsal et al. .................. | 429/482 |

FOREIGN PATENT DOCUMENTS

WO  WO2009146924  * 12/2009

* cited by examiner

*Primary Examiner* — Bach Dinh
(74) *Attorney, Agent, or Firm* — Cesari and McKenna, LLP

(57) ABSTRACT

An electrode for an electrochemical device includes a conductor, and an active layer formed on the conductor and including a polybenzimidazole polymer that contains at least one of the functional group of the following formula:

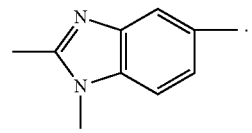

21 Claims, 12 Drawing Sheets

ELECTRODE FOR AN ELECTROCHEMICAL DEVICE AND METHOD FOR DETECTING HYDROGEN PEROXIDE USING THE ELECTRODE

CROSS-REFERENCE TO RELATED APPLICATION

This application claims priority of Taiwanese application No. 099125889, filed on Aug. 4, 2010, Taiwanese application No. 099125888, filed on Aug. 4, 2010, and Taiwanese application No. 099127939, filed on Aug. 20, 2010.

BACKGROUND OF THE INVENTION

1. Field of the Invention

This invention relates to a modified polybenzimidazole, a method for preparing the same, an electrode made from a polybenzimidazole compound, and a method for detecting hydrogen peroxide using the electrode.

2. Description of the Related Art

Polybenzimidazoles, characterized by great chemical stability, high thermal resistance, high mechanical strength, etc., are well known to be suitable for use in a separatory media, such as a filtration film or an ion exchange resin. The most serious problem for polybenzimidazoles is that they are soluble only in a solvent with high polarity, such as dimethylsulfoxide, N,N-dimethylacetamide, N,N-dimethylformamide, and N-methylpyrrolidinone. At present, methods for improving solubility of polybenzimidazoles include, e.g., introducing a flexible side chain or modifying the main chain structure of polybenzimidazoles.

U.S. Pat. No. 4,814,400 discloses novel polybenzimidazole esters, polybenzimidazole carboxylic acids, and methods for producing both. The methods include reacting polybenzimidazole polymers with halogenated alkyl esters to form polybenzimidazole esters and subsequently hydrolyzing the polybenzimidazole esters to form polybenzimidazole carboxylic acids. The polybenzimidazole esters and the polybenzimidazole carboxylic acids thus produced have a repeating unit represented by the following formula:

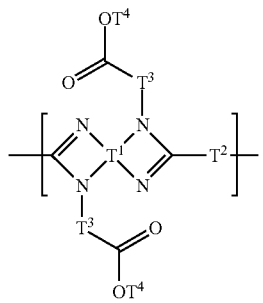

wherein $T^1$ is a tetravalent aromatic group, $T^2$ is arylene or alkylene, $T^3$ is a $C_1$ to $C_{22}$ alkylene group, and $T^4$ is hydrogen, a $C_1$ to $C_{20}$ alkylene group, a $C_1$ to $C_{20}$ alkenylene group, or a $C_1$ to $C_{20}$ arylene group.

In this U.S. patent, the method for producing polybenzimidazole carboxylic acid is a two-step procedure, which is complicated, and the solubility of the polybenzimidazole esters and the polybenzimidazole carboxylic acids are never addressed.

Therefore, there is a need in the art to provide a polybenzimidazole derivative having good solubility, and a relatively simple method for producing the same.

In the method for detecting hydrogen peroxide by virtue of an electrochemical device, an electrode used in the electrochemical device can be classified into enzyme electrode and non-enzyme electrode. An electrochemical device using an enzyme electrode has the advantage of superior specificity, but the stability and activity of the enzyme would be easily influenced by the environment and the duration of use. As to an electrochemical device using a non-enzyme electrode, an oxidation potential is usually measured in this device to determine the amount of hydrogen peroxide. Since the oxidation potential is susceptible to interference with other undesired substances in a test sample, the specificity for hydrogen peroxide is reduced and the accuracy of the test result would be adversely affected.

An electrode used for detecting hydrogen peroxide disclosed in U.S. Pat. No. 5,320,725 includes a testing surface and a transducing film covering the testing surface. The transducing film includes a cross-linked redox polymer network having a redox compound and a peroxidase chemically bonded to the redox polymer network. The method for detecting hydrogen peroxide disclosed in this patent includes: oxidizing peroxidase by virtue of hydrogen peroxide; reducing the oxidized peroxidase by oxidizing the redox compound of the redox polymer network; electroreducing the oxidized redox compound by electrons originated at the electrode; and measuring a generated current. Because the peroxidase of the transducing film is an enzyme, the electrode of this patent is not stable and is easily influenced by the environment, and the life span of the electrode is limited.

Therefore, there is a need in the art to provide an electrode for an electrochemical device which has good stability and high specificity for hydrogen peroxide.

SUMMARY OF THE INVENTION

Therefore, according to a first aspect, this invention provides a carboxylic polybenzimidazole containing at least one of the following functional group of formula (I):

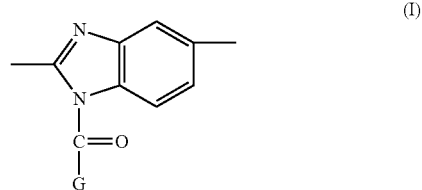

wherein G is a group containing a carboxylic acid end group or a carboxylated end group.

According to a second aspect, this invention provides a method for preparing a carboxylic polybenzimidazole including: reacting a polybenzimidazole polymer with a cyclic acid anhydride to form the carboxylic polybenzimidazole.

According to a third aspect, this invention provides an electrode for an electrochemical device, the electrode including a conductor and an active layer that is formed on the conductor and that includes a polybenzimidazole polymer containing at least one of the functional group of the following formula:

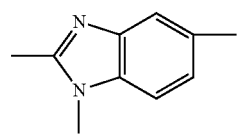

According to a fourth aspect, this invention provides a method for detecting hydrogen peroxide, including: contacting a test sample with the electrode as described in the aforesaid third aspect such that the polybenzimidazole polymer of the active layer of the electrode is oxidized; applying a constant voltage to the electrode to reduce the oxidized polybenzimidazole polymer of the active layer such that an electrical current is generated; and measuring the electrical current.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
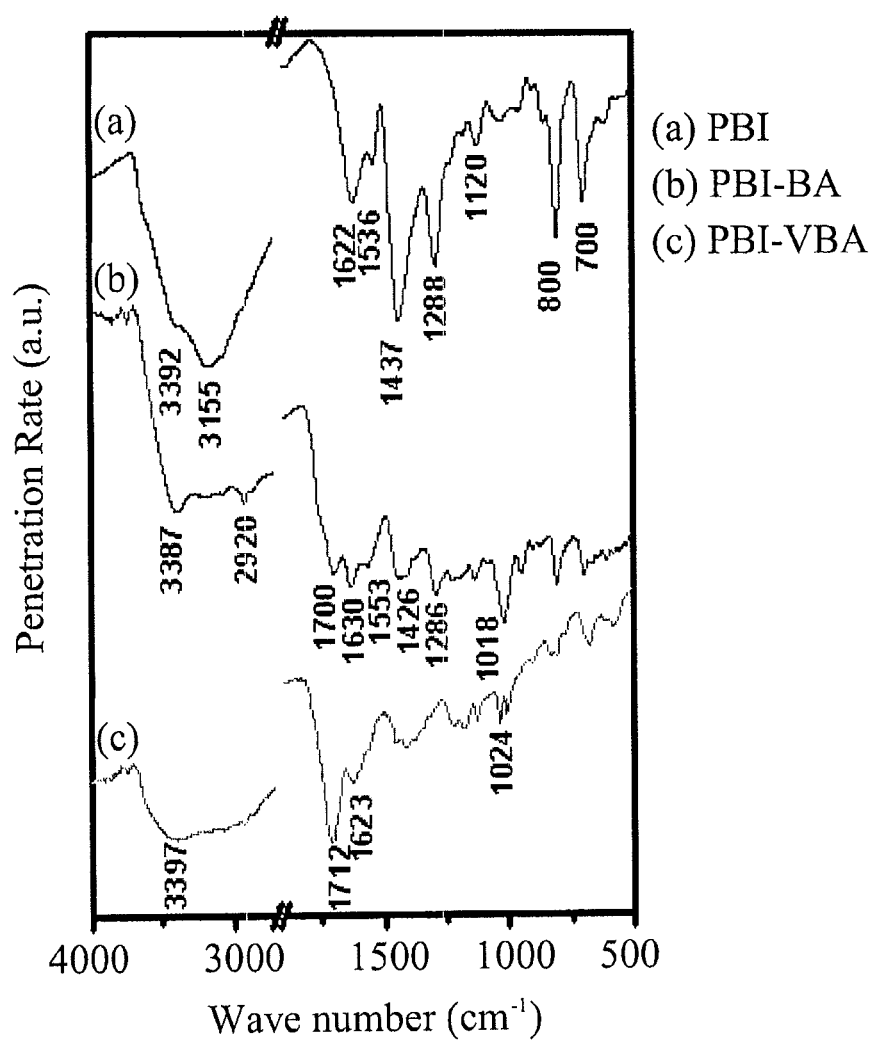
FIG. 1 is an infrared spectrum of carboxylic polybenzimidazoles of Preparation Example 1 (Curve a), Preparation Example 2 (Curve b) and Preparation Example 3 (Curve c)

A carboxylic polybenzimidazole according to the present invention includes at least one repeating unit represented by the following formula (I):

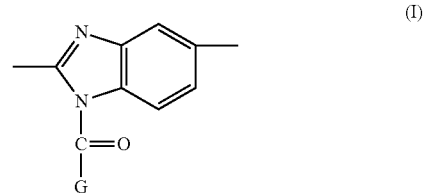

wherein G is a group containing a carboxylic acid end group or a carboxylated end group.

In particular, the carboxylic polybenzimidazole includes a repeating unit represented by the following formula (II):

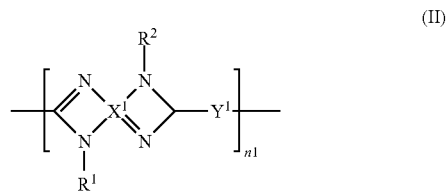

wherein $X^1$ is a tetravalent aromatic group including two phenyl groups, each of the phenyl groups being bonded with the nitrogen atoms in formula (II) to form a benzimidazole ring, $R^1$ and $R^2$ are independently hydrogen or —(C=O)-G, with the proviso that, in the repeating units of the carboxylic polybenzimidazole, at least one of $R^1$ or $R^2$ is —(C=O)-G, wherein G is —Z—COOM, Z being a $C_2$ to $C_{22}$ divalent aliphatic group, M being selected from the group consisting of hydrogen, lithium, sodium, potassium, and ammonium, $Y^1$ is a single bond, a $C_2$ to $C_{20}$ divalent aromatic group, a $C_2$ to $C_{20}$ divalent aliphatic group, or a $C_2$ to $C_{20}$ divalent alicyclic group, and n1 is an integer ranging from 10 to 1000.

Preferably, $X^1$ of the formula (II) is represented by the following formula:

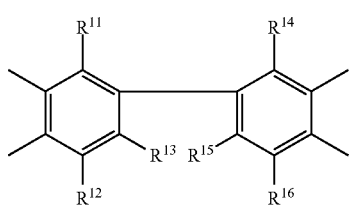

wherein $R^{11}$, $R^{12}$, $R^{13}$, $R^{14}$, $R^{15}$, and $R^{16}$ are independently hydrogen or halogen. In an embodiment of this invention, $R^{11}$, $R^{12}$, $R^{13}$, $R^{14}$, $R^{15}$, and $R^{16}$ are hydrogen.

Preferably, $Y^1$ of the formula (II) is selected from the group consisting of a single bond, methylene, ethylene, propylene, butylene, pentylene, hexylene, vinylene, propenylene, butenylene, hexenylene, cyclohexylene, cyclohexenylene, phenylene, pyridylene, furanylene, pyrazylene, pyranylene, and thiophenylene. In an embodiment of this invention, $Y^1$ is phenylene.

Preferably, Z of —(C=O)—Z—COOM of the formula (II) is a $C_2$ to $C_{22}$ alkyl group or a $C_2$ to $C_{22}$ alkenyl group, and may be optionally substituted with a substituent selected from the group consisting of —$CH_3$, —$(CH_3)_2$, —CH=$CH_2$, —CH=$CHCH_2$ $(CH_2)_{n3}CH_3$, —S—(C=O)—$CH_3$,

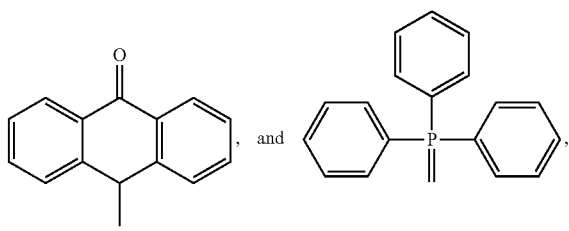

wherein n3 is an integer ranging from 4 to 18. In an embodiment of this invention, M is hydrogen, and Z is ethylene or vinylene.

Particularly, in the examples of the present invention, the carboxylic polybenzimidazole has a repeating unit represented by the following formula:

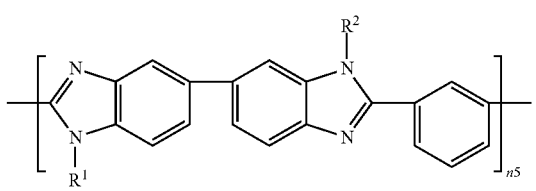

wherein n5 is an integer ranging from 10 to 1000. In an example of this invention, $R^1$ and $R^2$ are independently hydrogen or

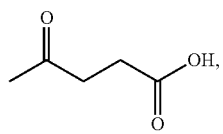

and, in the repeating units, at least one of $R^1$ and $R^2$ is

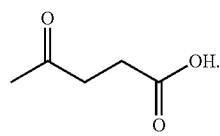

The polymer is named as poly[N-(1-one-butyric acid)benzimidazole] (PBI-BA). In another example of the present invention, $R^1$ and $R^2$ are independently hydrogen or

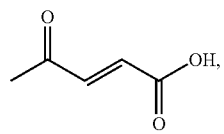

and, in the repeating units, at least one of $R^1$ and $R^2$ is

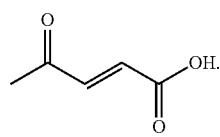

The polymer is named as poly[N-(1-one-2-vinyl-butyric acid)benzimidazole] (PBA-VBA).

Alternatively, the carboxylic polybenzimidazole according to the present invention may include a repeating unit represented by the following formula (III):

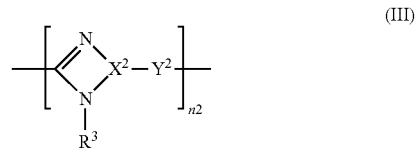

wherein $X^2$ is a trivalent aromatic group including a phenyl group that is bonded with the nitrogen atoms in formula (III) to form a benzimidazole ring, $R^3$ is hydrogen or —(C=O)-G, with the proviso that, in the repeating units of the carboxylic polybenzimidazole, at least one of $R^3$ is —(C=O)-G. In the formula (III), $Y^2$, G of $R^3$, and n2 have the same definitions as $Y^1$, G of $R^1$ and $R^2$, and n1 in formula (II).

Preferably, $X^2$ of formula (III) is represented by the following formula:

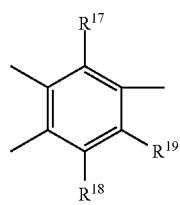

wherein $R^{17}$, $R^{18}$, and $R^{19}$ are independently hydrogen or halogen.

Preferably, $Y^2$ of formula (III) is selected from the group consisting of a single bond, methylene, ethylene, propylene, butylene, pentylene, hexylene, vinylene, propenylene, butenylene, hexenylene, cyclohexylene, cyclohexenylene, phenylene, pyridylene, furanylene, pyrazylene, pyranylene, and thiophenylene.

Preferably, Z of —(C=O)—Z—COOM of formula (III) is a $C_2$ to $C_{22}$ alkyl group or a $C_2$ to $C_{22}$ alkenyl group, and may be optionally substituted with a substituent selected from the group consisting of —$CH_3$, —$(CH_3)_2$, —CH=$CH_2$, —CH=$CHCH_2$ $(CH_2)_{n3}CH_3$, —S—(C=O)—$CH_3$,

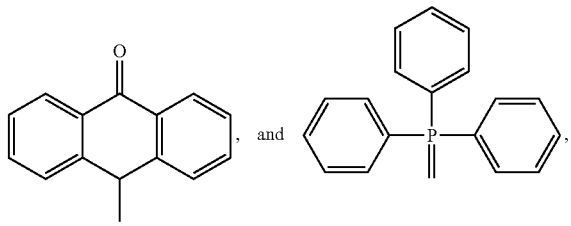 [SMILES: CC1c2ccccc2C(=O)c2ccccc21 ; C=P(c1ccccc1)(c1ccccc1)c1ccccc1]

, and wherein n3 is an integer ranging from 4 to 18. More preferably, in formula (III), M is hydrogen, and Z is ethylene or vinylene.

A method for preparing the aforesaid carboxylic polybenzimidazoles is provided below to aid one skilled in the art in synthesizing the carboxylic polybenzimidazoles, with more detailed examples in the following Example section.

The method includes reacting a polybenzimidazole polymer with a cyclic acid anhydride to form a carboxylic polybenzimidazole.

Preferably, the method includes: (a) dissolving a polybenzimidazole polymer in a solvent to form a polybenzimidazole solution; (b) reacting the polybenzimidazole polymer with a metal hydride to form a precursor; and (c) reacting the precursor with a cyclic acid anhydride to form the carboxylic polybenzimidazole.

More preferably, the reactions are conducted under a temperature ranging from 60° C. to 160° C. and for a time period ranging from 12 to 36 hours.

The polybenzimidazole polymer used in the method may include a repeating unit represented by the following formulas (V) or (VI):

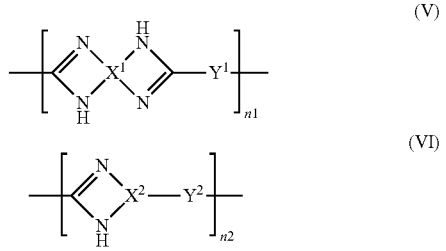

(V)

(VI)

wherein $X^1$, $Y^1$, and n1 in formula (V), and $X^2$, $Y^2$, and n2 in formula (VI) have the same definitions as $X^1$, $Y^1$, and n1 in formula (II) and $X^2$, $Y^2$, and n2 in formula (III).

In the examples of the present invention, the polybenzimidazole polymer includes a repeating unit represented by the following formula (VII):

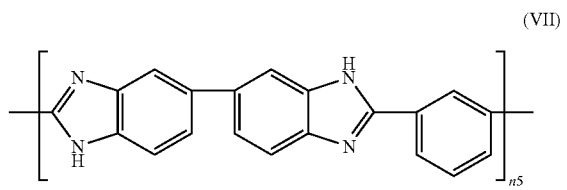

(VII)

wherein n5 is an integer ranging from 10 to 1000.

It should be noted that the polybenzimidazole polymer used in the method of the present invent ion may be prepared by any process known to those skilled in the art, for example, by the method disclosed in *J. Polym. Sci. Part A*, 2, 2605 (1964).

The solvent used to form the polybenzimidazole solution may be any one capable of dissolving the particular polybenzimidazole polymer. Preferably, the solvent is selected from the group consisting of dimethylsulfoxide (DMSO), N,N-dimethyllacetamide, N,N-dimethylformamide, and N-methylpyrrolidinone. In the examples of the present invention, the solvent is DMSO.

Preferably, the metal hydride is NaH, LiH, or KH, and the mole ratio of the metal hydride to the polybenzimidazole polymer ranges from 1:1 to 20:1. In the examples of the present invention, the metal hydride is NaH.

The precursor formed by reacting the polybenzimidazole polymer, e.g., the one containing formulas (V) or (VI), with the metal hydride may be represented by the following formulas:

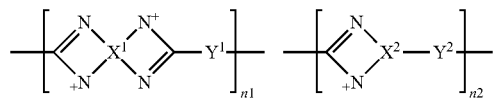

The cyclic acid anhydride may be represented by the following formula (IV):

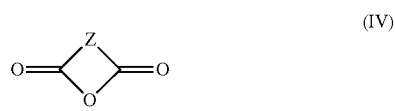

(IV)

wherein Z is a $C_2$ to $C_{22}$ divalent aliphatic group. In the examples of the present invention, Z of formula (IV) is ethylene or vinylene, i.e., the cyclic acid anhydride is succinic anhydride or maleic anhydride. Preferably, the mole ratio of the cyclic acid anhydride to the polybenzimidazole polymer ranges from 4:1 to 20:1.

In the present invention, the applicants provide an electrode including the polybenzimidazole polymer with uncarboxylated polybenzimidazole polymer (not containing a carboxyl group) or the aforesaid carboxylic polybenzimidazole polymer for use in detecting hydrogen peroxide.

The applicants found that the polybenzimidazole polymer can be directly or indirectly oxidized by hydrogen peroxide. By virtue of applying a voltage to reduce the oxidized polybenzimidazole polymer, an electrical current may be generated, and concentration of hydrogen peroxide may be calculated from the generated electrical current.

Particularly, the carboxylic polybenzimidazole polymer can be oxidized by hydrogen peroxide directly, while the uncarboxylated polybenzimidazole polymer can be oxidized by hydrogen peroxide indirectly in the presence of an organic acid. The organic acid is initially oxidized to a peroxy acid by hydrogen peroxide, and then the polybenzimidazole polymer is oxidized by the peroxy acid.

Therefore, an electrode used for an electrochemical device for detecting hydrogen peroxide according to the present invention includes a conductor, and an active layer formed on the conductor and including a polybenzimidazole polymer that contains at least one of the functional group represented by the following formula:

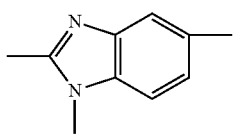

Particularly, the polybenzimidazole polymer of the active layer of the electrode may be a carboxylic polybenzimidazole which includes a repeating unit represented by the aforementioned formulas (II) or (III). In the examples of the present invention, the polybenzimidazole polymer used in the active layer is the aforementioned PBI-BA or PBI-VBA.

Alternatively, the polybenzimidazole polymer of the active layer of the electrode may include a repeating unit represented by the following formulas (II') or (III'):

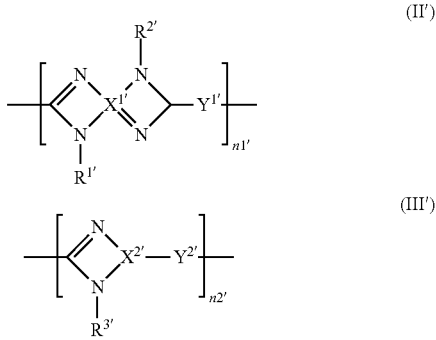

wherein $R^{1'}$, $R^{2'}$, and $R^{3'}$ are independently hydrogen or a $C_1$ to $C_{12}$ alkyl group, and $X^{1'}$, $Y^{1'}$, $n1'$, $X^{2'}$, $Y^{2'}$, and $n2'$ have the same definitions as $X^1$, $Y^1$, $n1$, $X^2$, $Y^2$, and $n2$ in the formulas (II) and (III). In other words, the polybenzimidazole polymer represented by the formulas (II') or (III') is an uncarboxylated polybenzimidazole polymer. In some examples of the present invention, the uncarboxylated polybenzimidazole polymer used in the active layer includes a repeating unit represented by the aforementioned formula (VII).

Preferably, the active layer that includes the uncarboxylated polybenzimidazole polymer further includes a material capable of providing an organic acidic group. In the examples of the present invention, the material is polyacrylic acid or an acid modified carbon nanotube containing a carboxyl group (i.e., —COOH or —(C=O)-A-COOH, in which A is $C_1$ to $C_8$ alkylene, $C_2$ to $C_8$ alkenylene, phenylene optionally substituted with at least one $C_1$ to $C_8$ alkyl group, or naphthylene optionally substituted with at least one $C_1$ to $C_8$ alkyl group). Preferably, the mole ratio of the polybenzimidazole polymer to the polyacrylic acid is adjusted to range from 0.05:1 to 2.9:1; and the weight ratio of the polybenzimidazole polymer to the acid modified carbon nanotube is adjusted to range from 0.3:1 to 24:1.

It should be noted that the electrode including an active layer containing the uncarboxylated polybenzimidazole polymer or the carboxylic polybenzimidazole polymer used in the present invention may be prepared by any conventional process known to those skilled in the art. In the examples of this invention, the electrodes are prepared by applying a pre-prepared polybenzimidazole polymer solution on a conductor and drying the same.

A method for detecting hydrogen peroxide uses the aforesaid electrode containing the uncarboxylated polybenzimidazole polymer or the carboxylic polybenzimidazole polymer according to the present invention, and includes: contacting a test sample with the electrode such that the polybenzimidazole polymer of the active layer of the electrode is oxidized; applying a constant voltage to the electrode to reduce the oxidized polybenzimidazole polymer of the active layer such that an electrical current is generated; and measuring the electrical current. Preferably, the constant voltage ranges from −0.6V to 0.1V.

Preferably, when the polybenzimidazole polymer of the active layer of the electrode contains a repeating unit represented by the aforementioned formulas (II') or (III') but not the material capable of providing an organic acidic group, the detection of hydrogen peroxide is conducted in the presence of an organic acid which may react with hydrogen peroxide. In the examples of the present invention, the organic acid is acetic acid.

Preferably, in addition to the electrode, an electrochemical device used in the present invention further includes a counter electrode, a reference electrode, a buffer, an ammeter, and any elements used for an electrochemical device known to those skilled in the art.

EXAMPLES

Preparation Example 1

PBI 2 grams (0.005 mole) of 3,3-diaminobenzidine tetrahydrochloride dihydrate was mixed with 53 grams of polyphosphoric acid, followed by heating to a temperature of 140° C. under an atmosphere of nitrogen and maintaining at this conditions for 2 hours. After complete dissolution of the 3,3-diaminobenzidine tetrahydrochloride dihydrate in the polyphosphoric acid, 1.03 grams (0.005 mole) of isophthaloyl dichloride was added, followed by heating to a temperature of 200° C., and reaction for 12 hours so as to form a reaction solution.

Subsequently, the reaction solution was mixed with deionized water and stirred at 60° C. for 2 hours. After removing a precipitate formed during stirring, a 1N $Na_2CO_3$ solution was added into the reaction solution, followed by stirring at 60° C. for 12 hours and filtration, thereby obtaining a dark brown precipitate. The precipitate was washed with deionized water and dissolved in dimethylsulfoxide (DMSO), followed by dropping a large amount of methanol, stirring for one day, and filtration and drying. A polybenzimidazole polymer (PBI) having a repeating unit represented by the following formula was acquired:

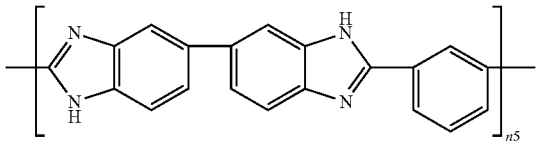

wherein n5 is an integer ranging from 10 to 1000.

Preparation Example 2

PEI-BA 0.3 gram ($9.7\times10^{-4}$ mole) of PBI produced from Preparation Example 1 was dissolved in 40 ml of DMSO so as to obtain a PBI solution. The PBI solution was heated to a temperature of 70° C., and was added with 0.47 gram (0.019 mole) of NaH, followed by reaction for 2 hours at 70° C. under an atmosphere of nitrogen so as to yield a precursor. 10 ml of succinic anhydride solution, produced by dissolving 3.8 grams (0.038 mole) of succinic anhydride in 10 ml of DNSO was added in the PBI solution, followed by heating to a temperature of 120° C., and reaction for 24 hours so as to obtain a reaction product. Acetone was subsequently dropped into the reaction product to precipitate a crude product. The crude product was dissolved in 10 ml of DMSO and added with 1N HCl aqueous solution to obtain a precipitate. The precipitate was refined by repeating the steps of dissolving in 10 ml of DMSO and adding with 1N HCl aqueous solution for several times so as to acquire refined PBI-BA. The reaction for producing PBI-BA is shown below:

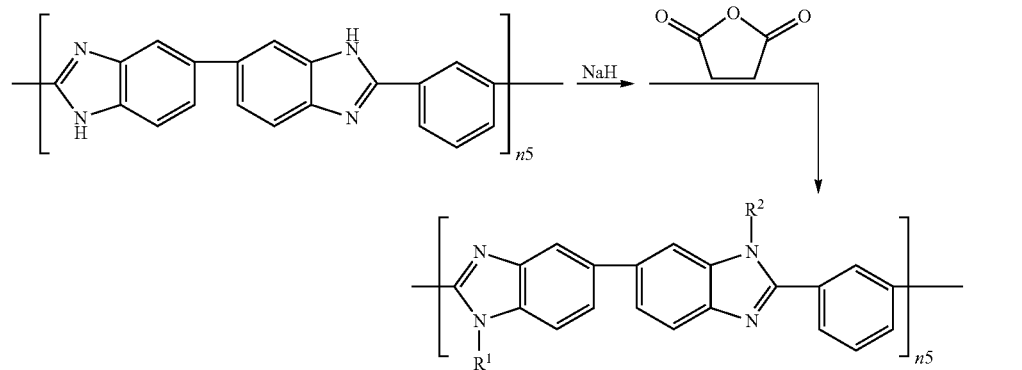

wherein $R^1$ and $R^2$ are independently hydrogen or

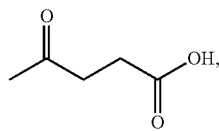

and, in the repeating units, at least one of $R^1$ and $R^2$ is

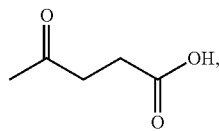

and n5 is an integer ranging from 10 to 1000.

Preparation Example 3

PBI-VBA

The steps for preparing PBI-VBA were similar to those of Preparation Example 2 except that the succinic anhydride solution was replaced by a maleic anhydride solution so as to yield a precipitate of PBI-VBA. The maleic anhydride solution was produced by dissolving 3.72 grams (0.038 mole) of maleic anhydride in 10 ml of DMSO. The PBI-VBA has a chemical formula similar to that of PBI-BA except that, in PBI-VBA, $R^1$ and $R^2$ are independently hydrogen or

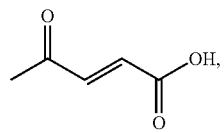

and, in the repeating units, at least one of $R^1$ and $R^2$ is

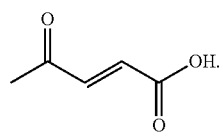

Evaluation of Physical Properties
Structure Identification
(1) Infrared Spectroscopic Analysis The structures of the PBI, PBI-BA, and PBI-VBA prepared from Preparation Examples 1 to 3 were analyzed using an infrared spectrometer. The spectra are shown in FIG. 1.

In the infrared spectrum (a) for PBI, characteristic peaks for PBI were found at 3415 cm$^{-1}$ typical for N—H, 3145 cm$^{-1}$ typical for N—H and C—H, 1622 cm$^{-1}$ typical for C=N and C=C, 1536 cm$^{-1}$ and 1437 cm$^{-1}$ typical for polybenzimidazole ring, 1288 cm$^{-1}$ typical for imidazole ring, and 800 cm$^{-1}$ and 700 cm$^{-1}$ typical for heterocyclic ring, which are similar to those disclosed in J. Mater. Chem., 9, 3045 (1999) and J. Membrane Sci., 280, 351 (2006).

In the infrared spectrum (b), the characteristic peak found at 1700 cm$^{-1}$ demonstrates the appearance of C=O of a carboxylic acid group, and the peak found at 1630 cm$^{-1}$ demonstrates the appearance of C=N, C=C, and C=O bonds that were generated from decyclizing succinic anhydride and bonding the decyclized succinic anhydride with a nitrogen atom in the polybenzimidazole ring. The aforesaid characteristic peaks verify the existence of PBI-BA.

In the infrared spectrum (c), the characteristic peak found at 1712 cm$^{-1}$ demonstrates the appearance of C=O of a carboxylic acid group, and the peak found at 1623 cm$^{-1}$ demonstrates the appearance of C=N, C=C, and C=O bonds that were generated from decyclizing maleic anhydride and bonding the decyclized maleic anhydride with a nitrogen atom in the polybenzimidazole ring. The aforesaid characteristic peaks verify the existence of PBI-VBA.

(2) X-ray Photoelectron Spectroscopy Analysis

Figure 2:
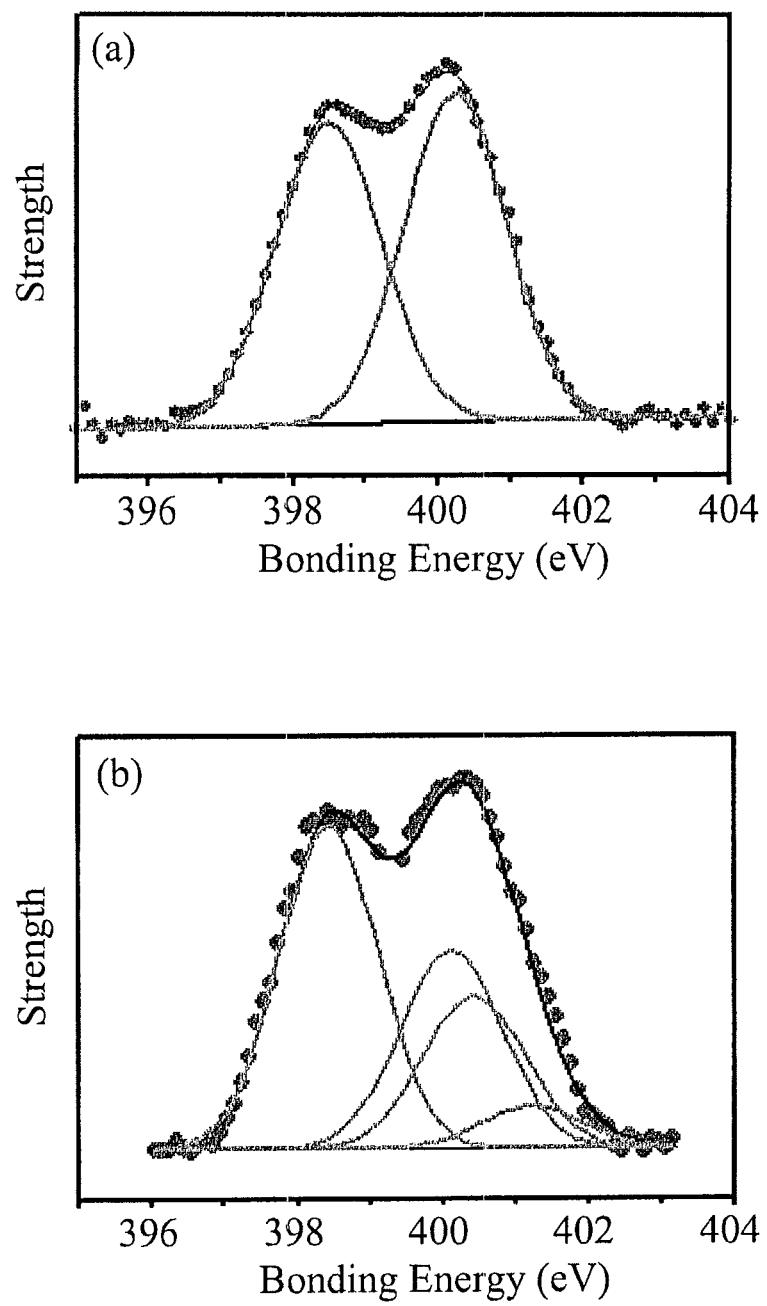
FIGS. 2(a) and (b) show XPS data demonstrating the N is peaks of PBI prepared by Preparation Example 1 and PBI-BA prepared by Preparation Example 2, respectively.

FIGS. 2(a) and 2(b) show XPS data demonstrating the N is peaks of PBI prepared by Preparation Example 1 and PBI-BA prepared by Preparation Example 2, respectively.

As shown in FIG. 2(a), two N is peaks were found at 398.4 eV and 400.2 eV, which respectively demonstrate nitrogen atoms of —N= and —NH— of imidazole. The area ratio of the two peaks is about 1:1.

As shown in FIG. 2(b), four N is peaks were found at 398.4, 400.2, 400.4, and 401.2 eV. As mentioned in FIG. 2(a), the peaks at 398.4 eV and 400.2 eV indicate nitrogen atoms of —N= and —NH— of imidazole, respectively. The peak at 400.4 eV demonstrates a nitrogen atom in a structure of

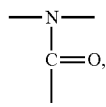

which resulted from bonding of —CO— of succinic anhydride to a nitrogen atom of —NH— of imidazole. The peak at 401.2 eV demonstrates a nitrogen atom of

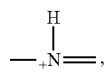

which resulted from oxidation of a nitrogen atom in the polybenzimidazole caused by 1N HCl aqueous solution used in preparation of PBI-BA. The grafting rate of the PBI-BA is 43.8% which is calculated from the area ratio of the peaks at 400.2 eV and 400.4 eV.

Solubility Analysis

An equal amount of each of the PBI, PBI-BA, and PBI-VBA prepared from Preparation Examples 1 to 3 was dissolved in various solutions listed in Table 1 and stirred for about 30 seconds. Solubility was observed through the naked eye and the results are shown in Table 1, in which "++" represents completely soluble, "+−" represents partially soluble and "−" represents insoluble. The solubility analysis was conducted at room temperature.

TABLE 1

|  | Solvent | | | | | |
| --- | --- | --- | --- | --- | --- | --- |
|  | Dimethyl-sulfoxide | Dimethyl-acetamide | Ac-etone | Ethanol | Meth-anol | Water |
| PBI (as a comparative example) | +− | ++ | − | − | − | − |
| PBI-BA | ++ | ++ | − | +− | +− | − |
| PBI-VBA | ++ | ++ | − | +− | ++ | +− |

As shown in Table 1, PBI-BA and PBI-VBA are completely soluble in dimethylsulfoxide and dimethylacetamide solutions and partially soluble in ethanol and methanol solutions. PBI-VBA is partially soluble in water. This reveals that the carboxylic polybenzimidazoles, PBI-BA and PBI-VBA, prepared according to the present invention have a superior solubility to that of PBI.

Contact Angle Analysis

A predetermined amount of each of the PBI, PBI-BA, and PBI-VBA prepared from the Preparation Examples 1 to 3 was dissolved in dimethylsulfoxide and applied onto a glass substrate, followed by drying the substrate so as to form a layer on the substrate. The contact angle was measured using contact angle analysis equipment by dropping a predetermined volume of water on each substrate. The results are shown in Table 2.

TABLE 2

|  | PBI | PBI-BA | PBI-VBA |
| --- | --- | --- | --- |
| Contact Angle | 72° | 56° | 53° |

As shown in Table 2, the contact angles of PBI-BA and PBI-VBA are smaller than that of PBI, which indicates that the PBI layer is more hydrophobic and the PBI-BA and PBI-VBA layers are more hydrophilic. In a liquid state electrochemical reaction, a more hydrophilic component generally has better electrochemical properties.

Thermogravimetric Analysis

Each of the PBI, PBI-BA, and PBI-VBA prepared from Preparation Examples 1 to 3 was heated from 50° C. to 700° C. at a heating rate of 20° C./min under an atmosphere of dry nitrogen in a chamber of a thermogravimetric analyzer (TGA) to determine weight loss thereof. The results are shown in Table 3. In Table 3, degraded yield indicates the residual weight at 700° C.

TABLE 3

|  | Initial Degraded Temperature (° C.) | Maximum Degraded Temperature (° C.) | Degraded Yield at 700° C. |
| --- | --- | --- | --- |
| PBI | 361 | 447 | 91.4% |
| PBI-BA | 219 | 347 | 68.1% |
| PBI-VBA | 217 | 358 | 61.7% |

PBI has the property of thermal resistance and thus the maximum degraded temperature of PBI is as high as about 447° C. After carboxylation, the coplanar structure of the main chain of the polybenzimidazole is twisted, resulting in lower maximum degraded temperatures of PBI-BA and PBI-VBA, i.e., 347° C. and 358° C. Nevertheless, the degraded temperatures of PBI-BA and PBI-VBA still meet commercial demands.

Preparation of Electrode Samples

Examples 1 to 10

A predetermined amount of each of the solutes, i.e., PBI, PBI-BA, and PBI-VBA, respectively prepared from Preparation Examples 1 to 3, and poly(N-butylbenzimidazole) (PBBI) was dissolved in 10 or 50 ml of dimethylsulfoxide (DMSO) solvent so as to obtain a sample solution. After the solute was completely dissolved, the sample solution was adjusted to 10 ml and have a concentration of 0.023 g/ml DMSO for subsequent use?. A predetermined amount of each of the sample solutions was uniformly applied onto an Au electrode serving as a conductor and having a surface area of 0.196 cm$^2$, followed by drying at 50° C. for 5 hours so as to obtain an electrode sample.

The amounts and species of the polybenzimidazoles, the amounts of dimethylsulfoxide (DMSO), and the amounts of the polybenzimidazole solutions applied onto the Au electrodes for each of the examples are shown in Table 4.

TABLE 4

| Example | Species of Polybenz-imidazole | Amount of Polybenzimidazole (grams/mole) | Amount of DMSO(ml) | Amount of Solution Applied(μl) |
| --- | --- | --- | --- | --- |
| 1 | PBI | 0.023/— | 50 | 2 |
| 2 | PBBI | 0.023/— | 10 | 2 |
| 3 | PBI-BA | 0.026/— | 10 | 15 |

TABLE 4-continued

| Example | Species of Polybenz-imidazole | Amount of Polybenzimidazole (grams/mole) | Amount of DMSO(ml) | Amount of Solution Applied(μl) |
|---|---|---|---|---|
| 4 | PBI-BA | 0.026/— | 10 | 10 |
| 5 | PBI-BA | 0.026/— | 10 | 5 |
| 6 | PBI-BA | 0.026/— | 10 | 1 |
| 7 | PBI-BA | 0.026/— | 10 | 0.5 |
| 8 | PBI-BA | 0.026/— | 10 | 0.25 |
| 9 | PBI-BA | 0.026/— | 10 | 0.125 |
| 10 | PBI-VBA | 0.05/— | 10 | 3 |

Example 11

0.06 gram ($1.95 \times 10^{-4}$ mole) of PBI prepared from Preparation Example 1 was dissolved in 10 ml of dimethylsulfoxide so as to obtain a PBI solution. 0.1 gram ($1.39 \times 10^{-3}$ mole) of polyacrylic acid, commercially available from SHOWA Corp. and having a molecular weight ranging from 8,000 to 12,000, was dissolved in 10 ml of dimethylsulfoxide so as to obtain a polyacrylic acid solution. 100 μl of the PBI solution and 320 μl of the polyacrylic acid solution were mixed, in which the mole ratio of PBI to polyacrylic acid was 0.07:1, so as to obtain a test solution. 1 μl of the test solution was uniformly applied on an Au electrode having a surface area of 0.196 cm$^2$ and serving as a conductor, followed by drying at 50° C. for 5 hours so as to obtain an electrode sample.

Example 12

0.02 gram of crude multi-wall carbon nanotube (MWCNT, S type, >99%, commercially available from Desunnano Co., Ltd.) were stirred with 60 ml of concentrated $H_2SO_4/HNO_3$ (3/1 v/v) for 15 min, followed by being incubated in a 43 kHz ultrasonic bath at 50° C. for 3 hours. The MWCNT solution was filtered through a 0.22-μm Millipore polyvinylidene fluoride membrane and was washed with deionized water until the pH thereof was approximate 7. The filtered solid was dried under vacuum for 12 hours so as to remove volatile components thereof and to form an acid modified carbon nanotube sample.

0.06 gram ($1.95 \times 10^{-4}$ mole) of PBI prepared from Preparation Example 1 was dissolved in 10 ml of dimethylsulfoxide so as to obtain a PBI solution. 0.1 gram of the acid modified carbon nanotube sample was dissolved in 10 ml of dimethylsulfoxide so as to form a carbon nanotube solution. 100 μl of the PBI solution and 1000 μl of the carbon nanotube solution were mixed, in which the weight ratio of PBI to carbon nanotube was 0.6:1, so as to obtain a test solution. 150 μl of the test solution was uniformly applied on an Au electrode having a surface area of 0.196 cm$^2$ and serving as a conductor, followed by drying at 50° C. for 5 hours so as to obtain an electrode sample.

Tests for Electrode Samples

Each of the electrode samples prepared from Examples 1 to 12 was disposed in 40 ml of phosphate buffer (pH 7.0) with an Au electrode serving as a counter electrode. Each of the electrodes and the counter electrode was independently connected to an ammeter using a conductive wire such that electrochemical sensors 1 to 12 were thus prepared.

Test 1: Measurement of Current Change Before and After Addition of $H_2O_2$

Figure 3:
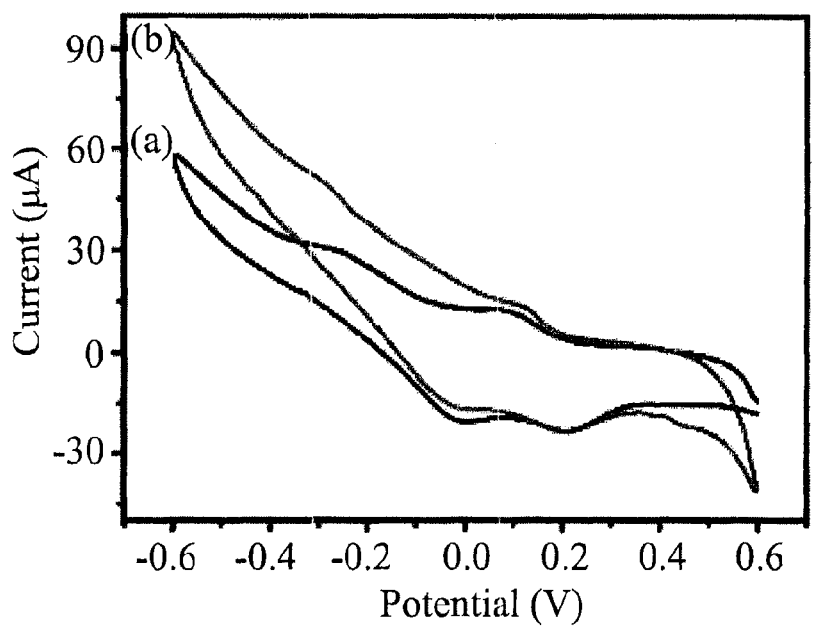
FIG. 3 shows the cyclic voltammograms of the electrochemical sensor containing an electrode of example 6 for detecting $H_2O_2$ according to the present invention with 3 mM $H_2O_2$ (Curve a) and without $H_2O_2$ (Curve b)

As shown in FIG. 3, cyclic voltammograms (a) and (b) of the electrochemical sensor 6 were recorded in a voltage ranging from −0.6V to 0.6V at a scan rate of 50 mV/s, in which curve (a) was recorded in the absence of $H_2O_2$, and curve (b) was recorded in the presence of 3 mM $H_2O_2$ solution. It reveals that, in FIG. 3, at negative potentials, the reducing current in curve (b) is higher than that in curve (a), indicating that the electrochemical sensor 6 containing the electrode of the present invention can be used to detect $H_2O_2$.

Test 2: Effect of Amount of Polybenzimidazole Solution Applied onto the Au Electrode on Detection of $H_2O_2$ A constant voltage of −0.5V was applied to the electrochemical sensors 3 to 9, and an initial current was recorded. After 150 seconds, 0.1 ml of 0.1 mM $H_2O_2$ solution was periodically added into the phosphate buffer of the electrochemical sensors 3 to 9 per 30 seconds. The current was recorded during the test and a highest current for each of the electrochemical sensors 3 to 9 was obtained. The current difference by subtracting the initial current from the highest current was calculated. The relationship between the current difference and the amount of the polybenzimidazole solution is plotted and is shown in FIG. 4.

Figure 4:
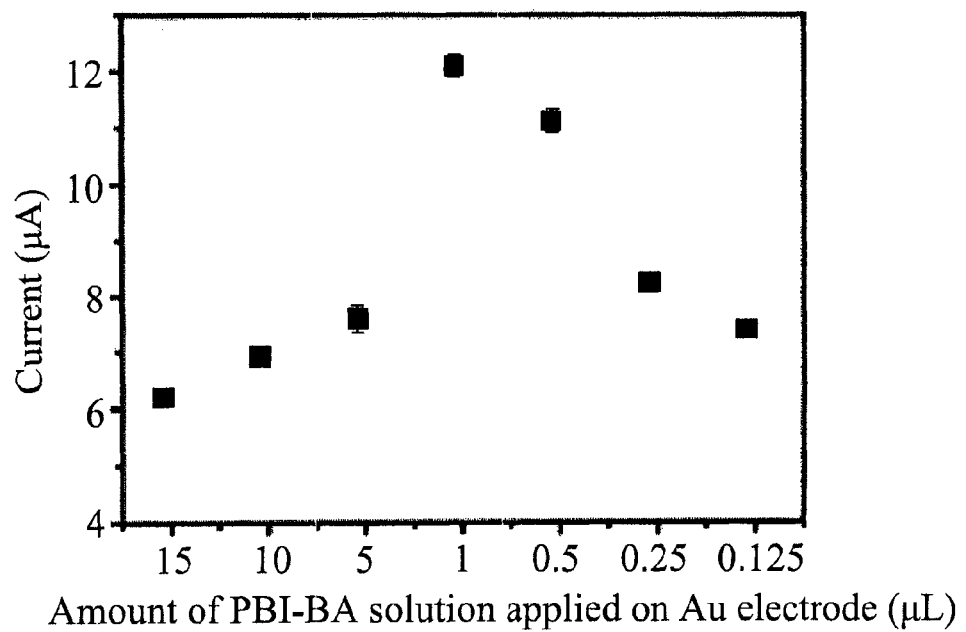
FIG. 4 is a plot of current vs. amount of PBI-BA solution applied on Au elect rode.

As shown in FIG. 4, electrochemical sensor 6 with 1 μl polybenzimidazole solution exhibits the highest current difference, which indicates that the proper amount for PBI-BA used in the electrode of the electrochemical sensor is 1 μl.

Test 3: Relationship Between Current Change and Concentration of $H_2O_2$ Solution and Effect of the Amount of Acetic Acid on Detection of $H_2O_2$ A constant voltage of −0.5V was applied to the electrochemical sensors 1, 2, 6, and 10 to 12, and an initial current was stabilized for 150 seconds. 0.1 ml of different concentrations of $H_2O_2$ solution was sequentially added into each of the electrochemical sensors 1, 2, 6, and 10 to 12, at a time period of 30 seconds. The current during the test was recorded, and the relationship between the current and time was plotted.

It should be noted that, since the electrode of each of the electrochemical sensors 1 and 2 was made from the uncarboxylated polybenzimidazole polymer, an organic acid should be added in the phosphate buffer for redox reaction. In the examples of this invention, acetic acid was used. In addition, the effect of the concentration of acetic acid on detection of $H_2O_2$ was also studied. For this study, different amounts of an acetic acid solution were added in the phosphate buffer before the test was conducted. The species of polybenzimidazole, the amount of acetic acid, and the concentration of $H_2O_2$ solution added in the phosphate buffer of each of the electrochemical sensors 1, 2, 6, 10 to 12 are shown in Table 5.

The results for the relationship between the current change vs. the concentration of $H_2O_2$ solution and the effect of the concentration of acetic acid on detection of $H_2O_2$ are shown in FIGS. 5 to 14 and Table 6.

In this test, response time for each of the electrochemical sensors 1, 2, 6, and 10 to 12 was also estimated, which was the time between the stage of current change and the next stage of current change. Shorter response time is desirable. The sensitivity for $H_2O_2$ was also studied and was a ratio of the slope of the curve of the current vs. $H_2O_2$ concentration plot to the surface area of the Au electrode.

TABLE 5

| Sensor | Species of poly-benzimidazole | Amount of Acetic Acid (ml) | Concentration of $H_2O_2$ solution added in the phosphate buffer (mM) |
|---|---|---|---|
| 1 | PBI | 0.1 | 0.075-0.5 |
|   |   | 0.5 | 0.0125-5.0 |
|   |   | 2.0 | 0.225-27.5 |
| 2 | PBBI | 0.1 | 0.02-10.0 |
|   |   | 0.5 | 0.02-15.0 |
|   |   | 2.0 | 0.2-22.5 |
| 6 | PBI-BA | — | 0.0125-7.5 |
| 10 | PBI-VBA | — | 0.0125-7.5 |

TABLE 5-continued

| Sensor | Species of polybenzimidazole | Amount of Acetic Acid (ml) | Concentration of $H_2O_2$ solution added in the phosphate buffer (mM) |
|---|---|---|---|
| 11 | PBI + polyacrylic acid | — | 0.025-10.0 |
| 12 | PBI + acid modified carbon nanotube | — | 0.025-10.0 |

TABLE 6

Figure 5:
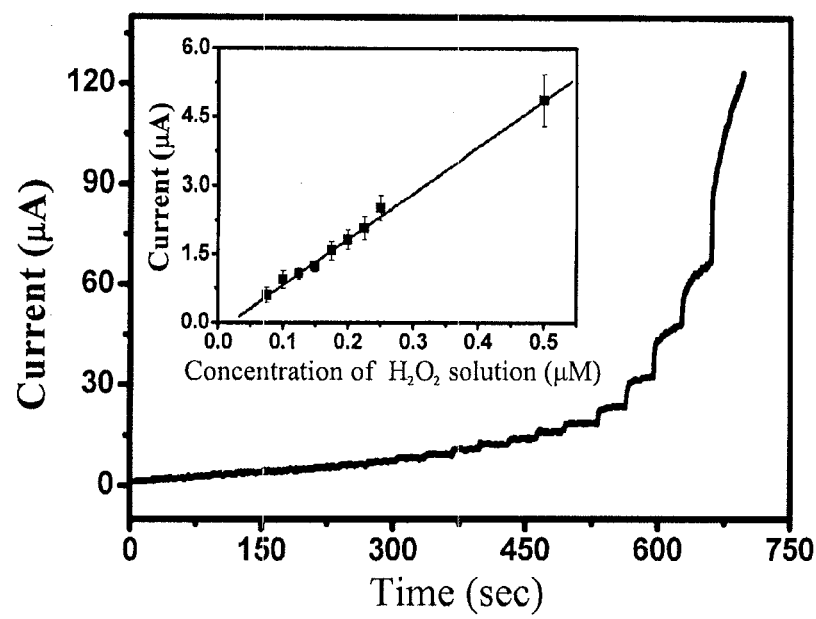
FIG. 5 shows plots of current vs. time and of current vs. concentration of $H_2O_2$ solution measured using an electrochemical sensor containing an electrode of Example 1 in the presence of 0.1 ml of acetic acid.
Figure 6:
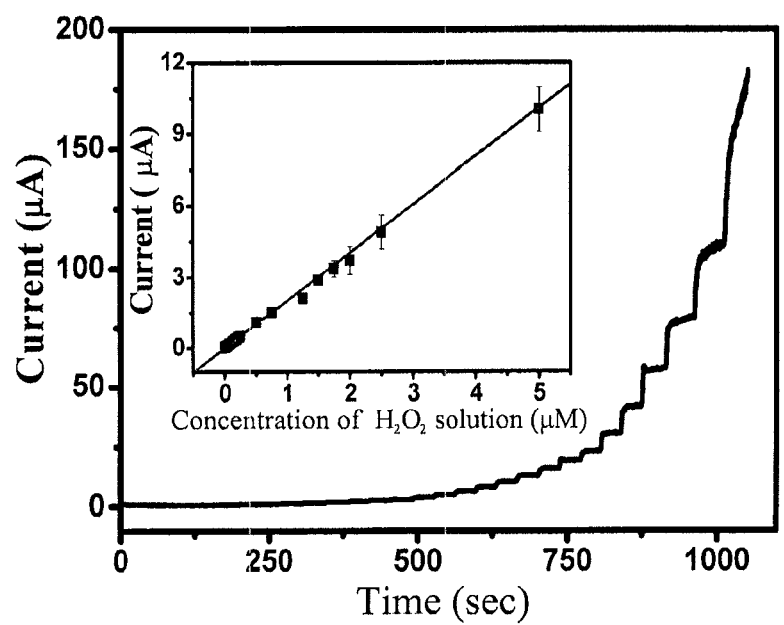
FIG. 6 shows plots of current vs. time and of current vs. concentration of $H_2O_2$ solution measured using an electrochemical sensor containing an electrode of Example 1 in the presence of 0.5 ml of acetic acid.
Figure 7:
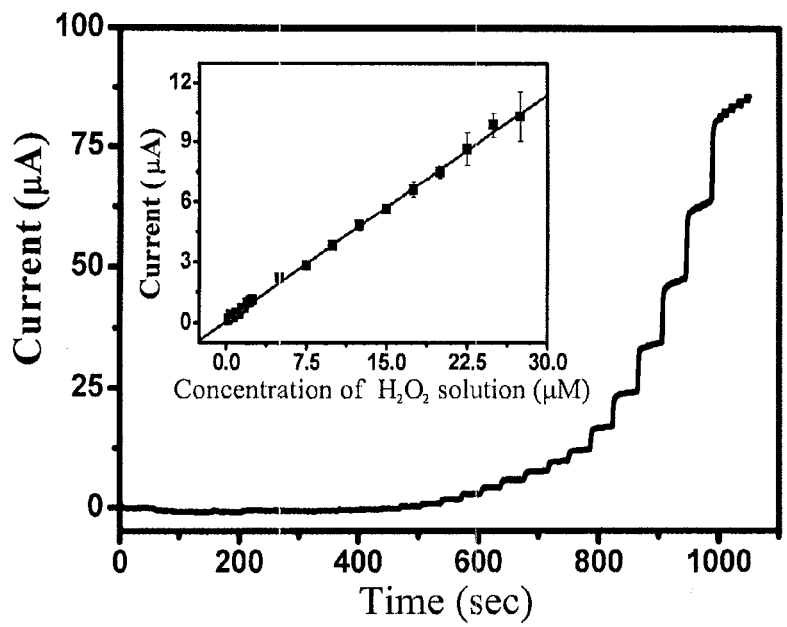
FIG. 7 shows plots of current vs. time and of current vs. concentration of $H_2O_2$ solution measured using an electrochemical sensor containing an electrode of Example 1 in the presence of 2.0 ml of acetic acid.
Figure 8:
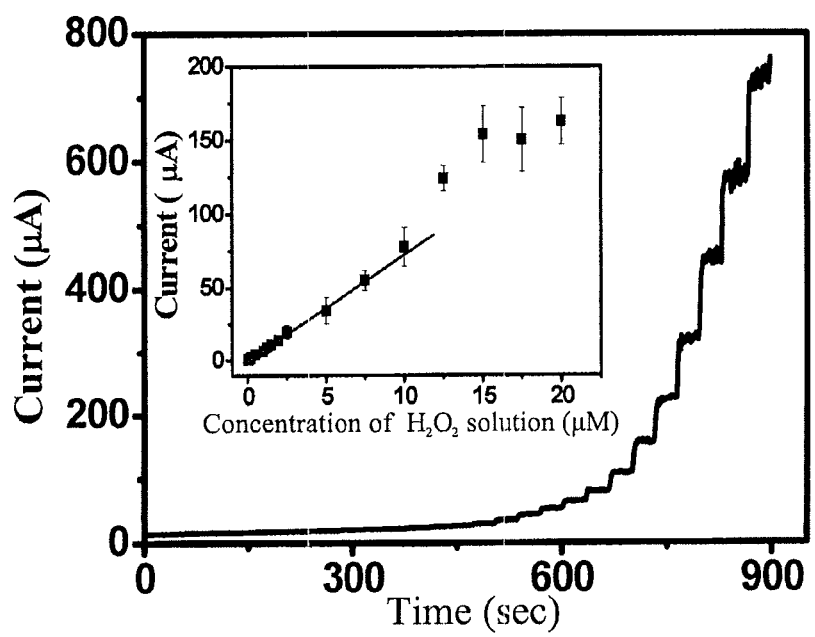
FIG. 8 shows plots of current vs. time and of current vs. concentration of $H_2O_2$ solution measured using an electrochemical sensor containing an electrode of Example 2 in the presence of 0.1 ml of acetic acid.
Figure 9:
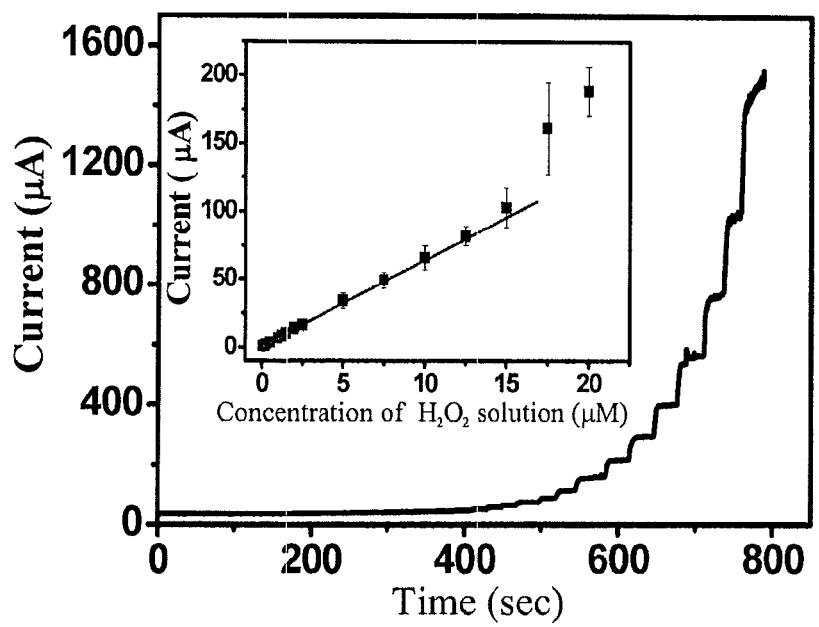
FIG. 9 shows plots of current vs. time and of current vs. concentration of $H_2O_2$ solution measured using an electrochemical sensor containing an electrode of Example 2 in the presence of 0.5 ml of acetic acid.
Figure 10:
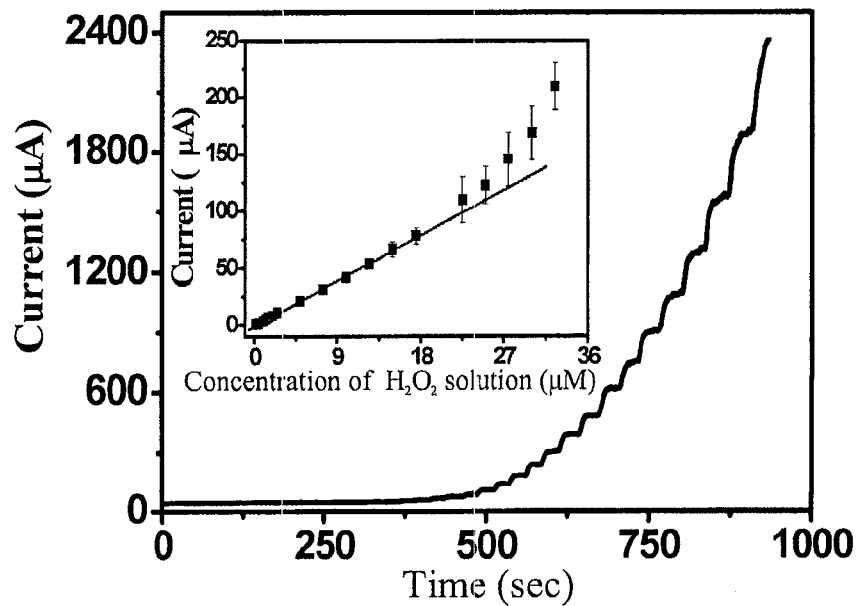
FIG. 10 shows plots of current vs. time and of current vs. concentration of $H_2O_2$ solution measured using an electrochemical sensor containing an electrode of Example 2 added with yet another amount of acetic acid in the presence of 2.0 ml of acetic acid.
Figure 11:
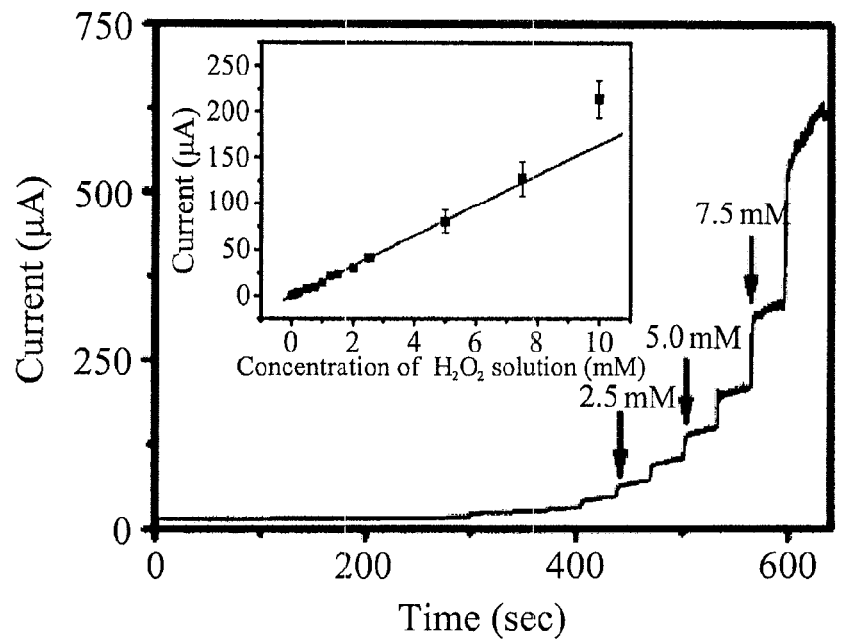
FIG. 11 shows plots of current vs. time and of current vs. concentration of $H_2O_2$ solution measured using an electrochemical sensor containing an electrode of Example 6.
Figure 12:
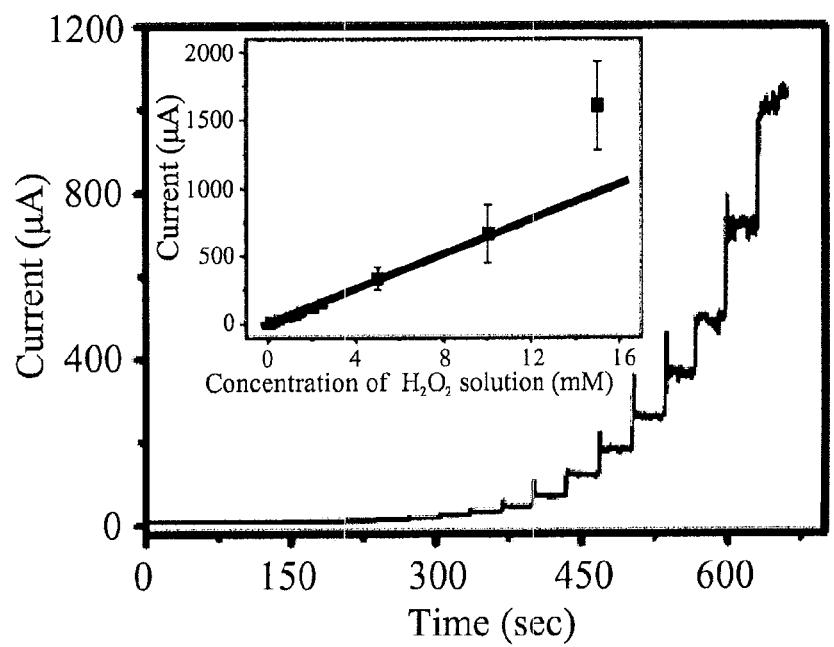
FIG. 12 shows plots of current vs. time and of current vs. concentration of $H_2O_2$ solution measured using an electrochemical sensor containing an electrode of Example 10.
Figure 13:
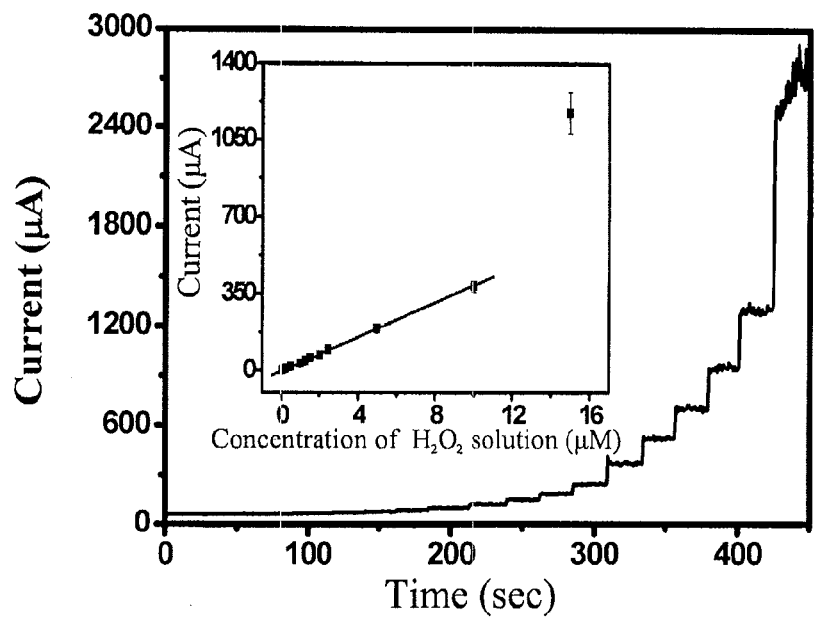
FIG. 13 shows plots of current vs. time and of current vs. concentration of $H_2O_2$ solution measured using an electrochemical sensor containing an electrode of Example 11.
Figure 14:
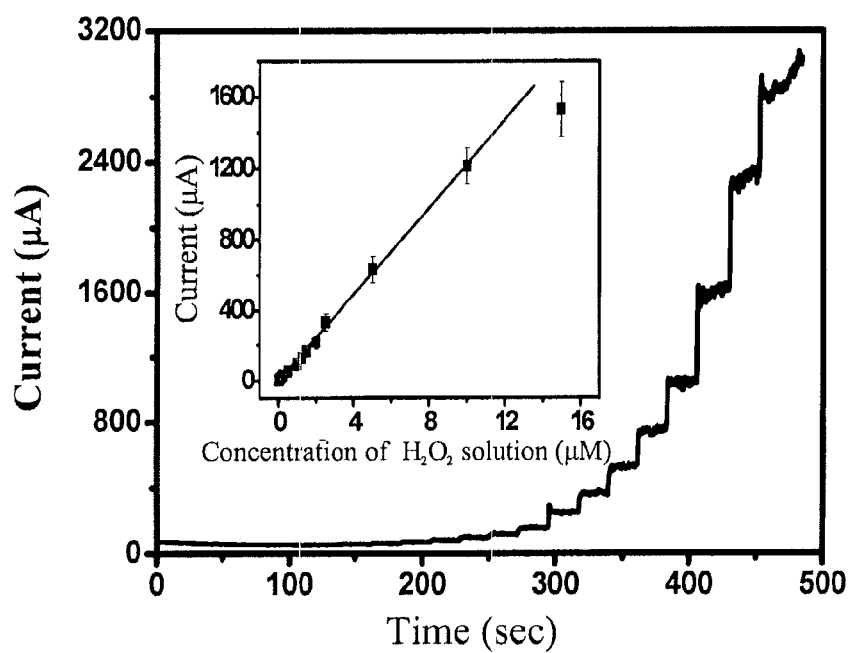
FIG. 14 shows plots of current vs. time and of current vs. concentration of $H_2O_2$ solution measured using an electrochemical sensor containing an electrode of Example 12.

| Sensor | Corresponding Figure | Response Time (sec) | Sensitivity ($\mu A/mM \cdot cm^2$) | Minimum Detectable Concentration of $H_2O_2$ ($\mu M$) |
|---|---|---|---|---|
| 1 | FIG. 5 | 7.8 | 51.4 | 12.50 |
|   | FIG. 6 | 6.3 | 10.3 | 6.25 |
|   | FIG. 7 | 4.0 | 1.9 | 75.00 |
| 2 | FIG. 8 | 11.3 | 35.1 | 6.25 |
|   | FIG. 9 | 6.0 | 33.2 | 12.50 |
|   | FIG. 10 | 4.9 | 21.9 | 75.00 |
| 6 | FIG. 11 | 9.8 | 72.0 | 12.50 |
| 10 | FIG. 12 | 2.3 | 265.3 | 12.50 |
| 11 | FIG. 13 | 2.2 | 182.0 | 12.50 |
| 12 | FIG. 14 | 2.7 | 569.4 | 6.25 |

As shown in FIGS. 5 to 14, the current may be increased with an increase in the $H_2O_2$ concentration, which demonstrates that polybenzimidazole polymer can be used in an electrode of an electrochemical device for $H_2O_2$ detection. Moreover, as shown in Table 5, the electrode with PBI and the acid modified carbon nanotube and the electrode with PBI-VBA exhibit superior response time and sensitivity, and the lower minimum detectable concentration of $H_2O_2$.

In addition, as shown in Table 5, although response time may be reduced with the increase in the concentration of acetic acid, the sensitivity is adversely influenced. Thus, the amount of the acetic acid should be properly adjusted. In this embodiment, the optimal amount of the acetic acid for sensors 1 and 2 are respectively 0.5 and 0.1 ml.

Test 4: Stability at High Temperature

Figure 15:
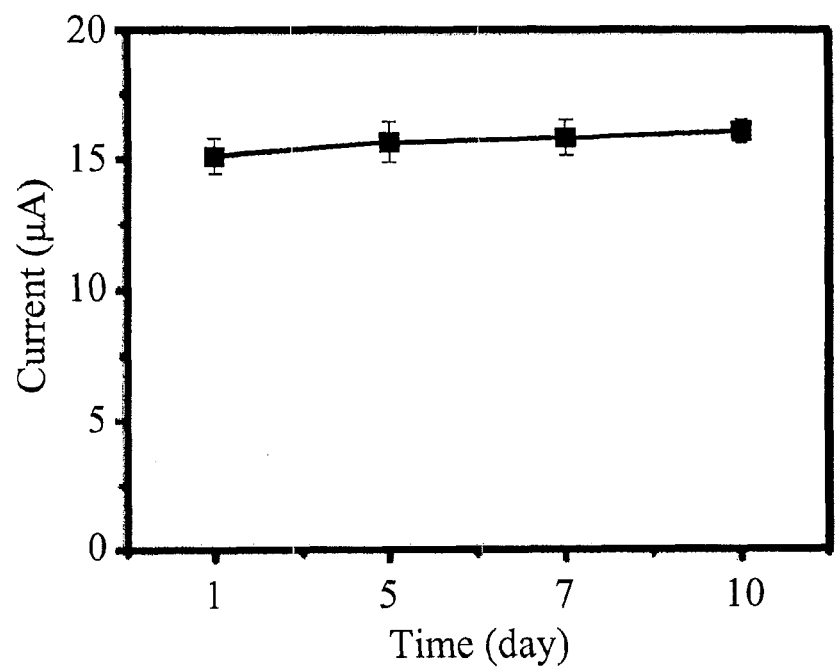
FIG. 15 is a plot of current vs. time illustrating the stability of the electrochemical sensor 6 containing an electrode of Example at high temperature.
Figure 16:
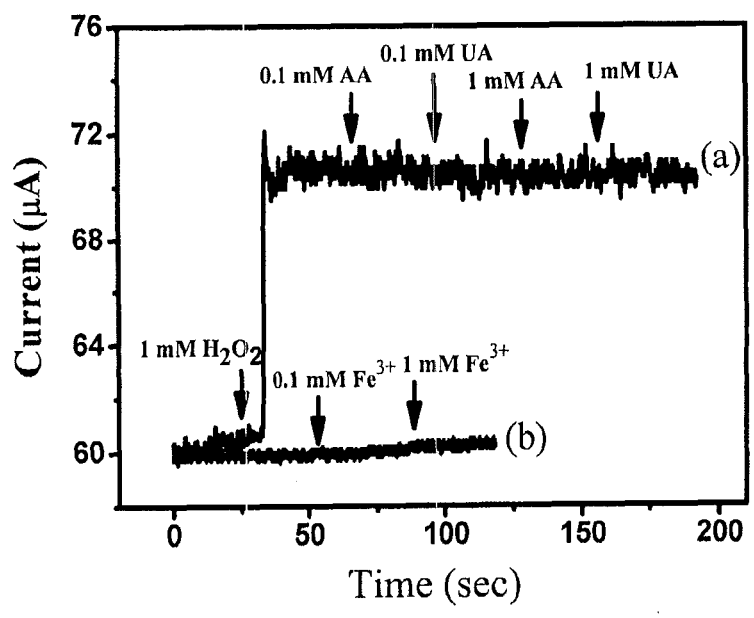
FIG. 16 is a plot of current vs. time illustrating the interference test results measured using an electrochemical sensor containing an electrode of Example 1.
Figure 17:
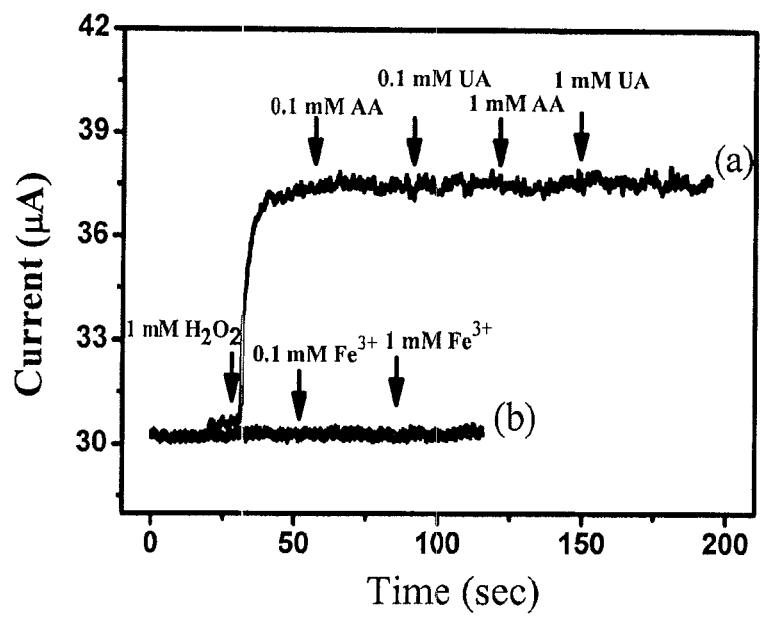
FIG. 17 is a plot of current vs. time illustrating the interference test results measured using an electrochemical sensor containing an electrode of Example 2.
Figure 18:
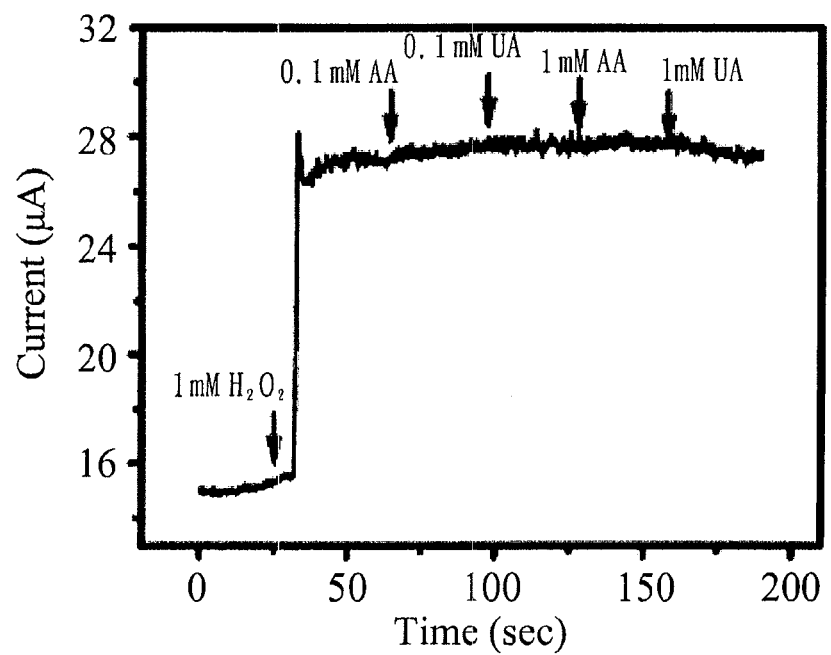
FIG. 18 is a plot of current vs. time illustrating the interference test results measured using an electrochemical sensor containing an electrode of Example 6.
Figure 19:
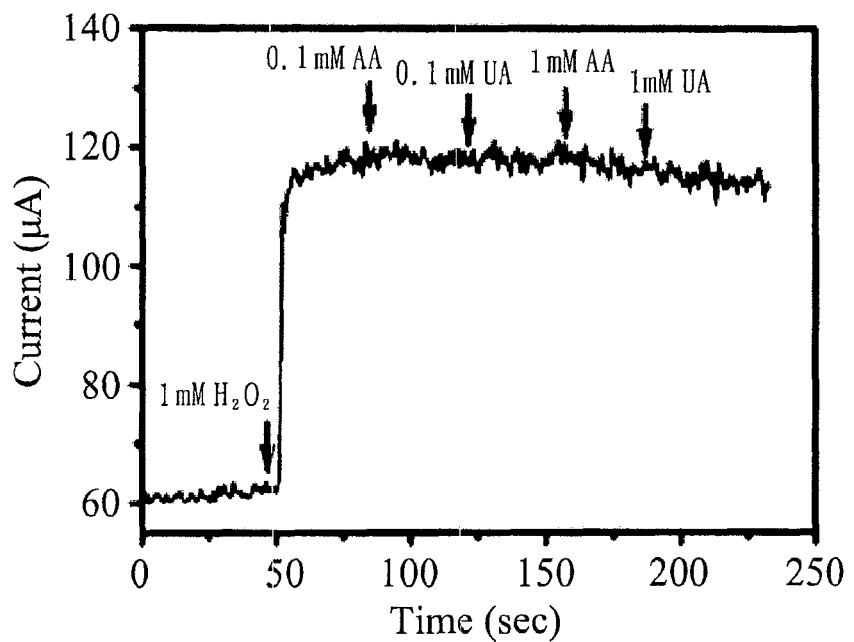
FIG. 19 is a plot of current vs. time illustrating the interference test results measured using an electrochemical sensor containing an electrode of Example 10.
Figure 20:
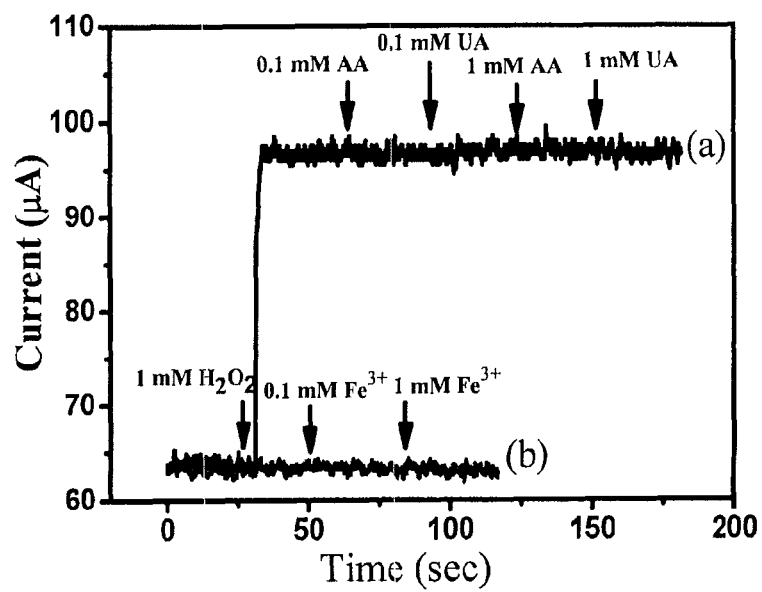
FIG. 20 is a plot of current vs. time illustrating the interference test results measured using an electrochemical sensor containing an electrode of Example 11.
Figure 21:
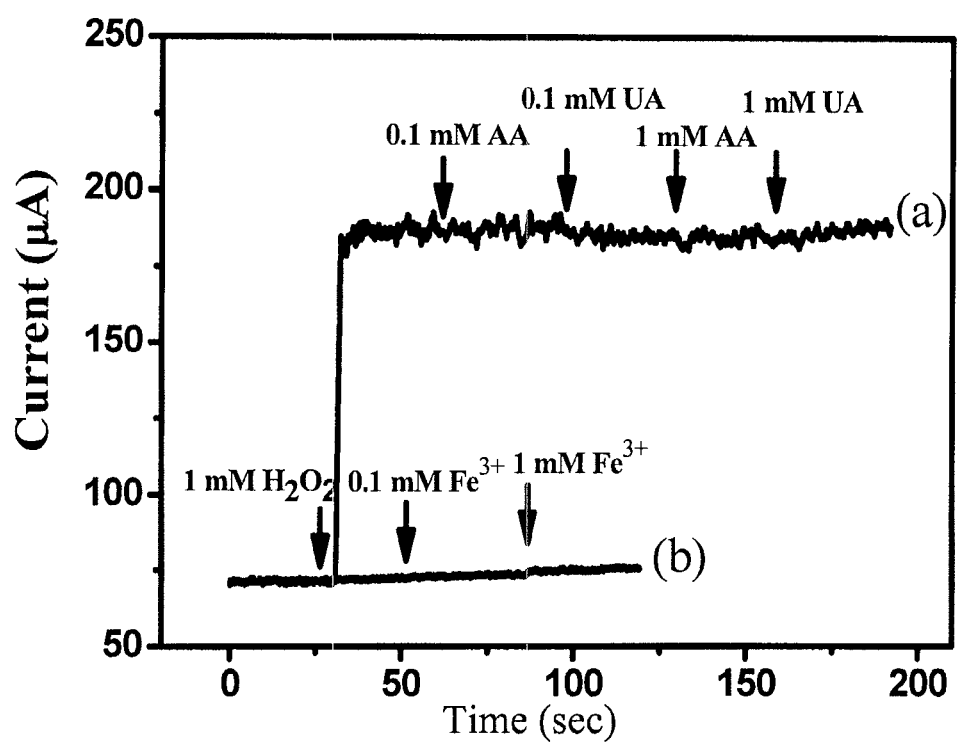
FIG. 21 is a plot of current vs. time illustrating the interference test results measured using an electrochemical sensor containing an electrode of Example 12.

An electrode prepared from Example 6 was disposed in an oven at a temperature of 100° C. At days 1, 5, 7, and 10, the electrode was taken out from the oven and used to detect 1 mM of $H_2O_2$ solution at −0.5V. The current was recorded. The results are as shown in FIG. 15. FIG. 15 reveals that there is no significant change among days 1, 5, 7, and 10. Thus, the electrode of this invention has good heat resistance and stability.

Interference Test 1: Vitamin C and Uric Acid

A constant voltage of −0.5V was applied to the electrochemical sensors 1, 2, 6, and 10 to 12, and an initial current was stabilized for 150 seconds. 1 mM $H_2O_2$ solution was added in the phosphate buffer of the electrochemical sensors 1, 2, 6, and 10 to 12. After the current is stabilized, test samples for interference, i.e., 0.1 mM Vitamin C (AA), 0.1 mM uric acid (UA), 1.0 mM Vitamin C, and 1.0 mM uric acid, were added in sequence to each of the electrochemical sensors 1, 2, 6, and 10 to 12. The current during the test was recorded. The results for the electrochemical sensors 1, 2, 6, and 10 to 12 are shown in curves (a) of FIGS. 16 to 21 respectively.

According to the curves (a) of FIGS. 16 to 21, there is no significant change in current after the addition of the test samples, which indicates that the electrode of the electrochemical sensor of the present invention exhibits great specificity for hydrogen peroxide.

Interference Test 2: Oxidant

The interference test 1 was repeated except that no $H_2O_2$ solution was added and the interference samples are replaced by 0.1 mM and 1.0 mM red prussiate-phosphate buffer prepared by dissolving red prussiate in phosphate buffer. The interference test 2 for oxidant was conducted on the electrochemical sensors 1, 2, 11, and 12 for verifying the response of the sensors for the interference samples in the absence of $H_2O_2$. The results are shown in curves (b) of FIGS. 16, 17, 20, and 21. It is confirmed that the electrochemical sensors of the present invention are not oxidized by the interference samples and thus no response current was measured.

In conclusion, a carboxylic polybenzimidazole may be produced by reacting a polybenzimidazole polymer with a cyclic anhydride according to the present invention. The carboxylic polybenzimidazole has an improved solubility in various solvents. Moreover, the method for preparing the carboxylic polybenzimidazole is relatively simple.

The electrode including an active layer of polybenzimidazole polymer or carboxylic polybenzimidazole polymer of the present invention exhibits great sensitivity, specificity and stability for detecting hydrogen peroxide. The concentration of hydrogen peroxide may be effectively investigated by an electrochemical sensor including the electrode of this invention.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

What is claimed is:

1. An electrode for determining the $H_2O_2$ concentration in a liquid sample, the electrode comprising:
    a conductor; and
    an active layer formed on said conductor and including a polybenzimidazole polymer that contains at least one of the functional group of the following formula:

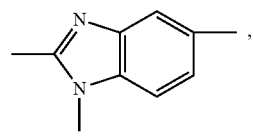

wherein said polybenzimidazole polymer contains a repeating unit represented by the following formula:

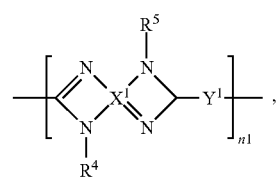

in which
$X^1$ is a tetravalent aromatic group including two phenyl groups, each of said phenyl groups is bonded with the nitrogen atoms in said formula to form two benzimidazole rings;

each of $R^4$ and $R^5$, independently, is hydrogen, a $C_1$ to $C_{12}$ alkyl group, or —(C=O)—Z—COOM, Z being ethylene or vinylene, and M being hydrogen;

$Y^1$ is a single bond, a $C_2$ to $C_{20}$ divalent aromatic group, a $C_2$ to $C_{20}$ divalent aliphatic group, or a $C_2$ to $C_{20}$ divalent alicyclic group; and n1 is an integer ranging from 10 to 1000.

2. The electrode of claim 1, wherein $X^1$ is represented by the following formula:

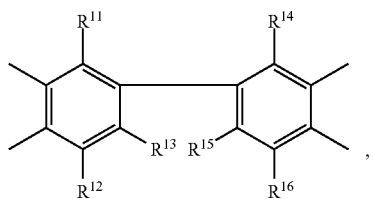

in which each of $R^{11}$, $R^{12}$, $R^{13}$, $R^{14}$, $R^{15}$, and $R^{16}$, independently, is hydrogen or halogen.

3. The electrode of claim 1, wherein $Y^1$ is selected from the group consisting of a single bond, methylene, ethylene, propylene, butylene, pentylene, hexylene, vinylene, propenylene, butenylene, hexenylene, cyclohexylene, cyclohexenylene, phenylene, pyridylene, furanylene, pyrazylene, pyranylene, and thiophenylene.

4. The electrode of claim 1, wherein each of $R^4$ and $R^5$, independently, is hydrogen or a $C_1$ to $C_{12}$ alkyl group.

5. The electrode of claim 4, wherein said active layer further includes a material capable of providing an organic acidic group.

6. The electrode of claim 5, wherein said material is polyacrylic acid or an acid modified carbon nanotube.

7. The electrode of claim 6, wherein the mole ratio of said polybenzimidazole polymer to said acrylic acid ranges from 0.05:1 to 2.9:1.

8. The electrode of claim 6, wherein the weight ratio of said polybenzimidazole polymer to said acid modified carbon nanotube ranges from 0.3:1 to 24:1.

9. An electrode for determining the $H_2O_2$ concentration in a liquid sample, the electrode comprising:
a conductor; and
an active layer formed on said conductor and including a polybenzimidazole polymer that contains at least one of the functional group of the following formula:

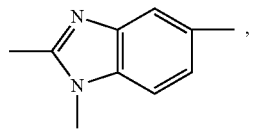

wherein said polybenzimidazole polymer contains a repeating unit represented by the following formula:

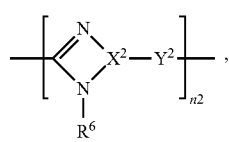

in which $X^2$ is a trivalent aromatic group including a phenyl group that is bonded with the nitrogen atoms in the formula to form a benzimidazole ring;

$R^6$ is hydrogen, a $C_1$ to $C_{12}$ alkyl group, or —(C=O)—Z—COOM, Z being ethylene or vinylene, and M being hydrogen;

$Y^2$ is a single bond, a $C_2$ to $C_{20}$ divalent aromatic group, a $C_2$ to $C_{20}$ divalent aliphatic group, or a $C_2$ to $C_{20}$ divalent alicyclic group; and n2 is an integer ranging from 10 to 1000.

10. The electrode of claim 9, wherein $X^2$ is represented by the following formula:

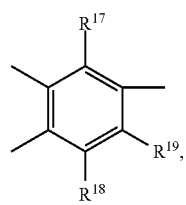

in which each of $R^{17}$, $R^{18}$, and $R^{19}$, independently, is hydrogen or halogen.

11. The electrode of claim 10, wherein $Y^2$ is a single bond, methylene, ethylene, propylene, butylene, pentylene, hexylene, vinylene, propenylene, butenylene, hexenylene, cyclohexylene, cyclohexenylene, phenylene, pyridylene, furanylene, pyrazylene, pyranylene, or thiophenylene.

12. The electrode of claim 9, wherein $R^6$ is hydrogen or a $C_1$ to $C_{12}$ alkyl group.

13. The electrode of claim 12, wherein said active layer further includes a material capable of providing an organic acidic group.

14. The electrode of claim 13, wherein said material is polyacrylic acid or an acid modified carbon nanotube.

15. The electrode of claim 14, wherein the mole ratio of said polybenzimidazole polymer to said acrylic acid ranges from 0.05:1 to 2.9:1.

16. The electrode of claim 14, wherein the weight ratio of said polybenzimidazole polymer to said acid modified carbon nanotube ranges from 0.3:1 to 24:1.

17. A method for detecting hydrogen peroxide, comprising:
contacting a test sample with an electrode of claim 1 such that the polybenzimidazole polymer of the active layer of the electrode is oxidized;
applying a constant voltage to the electrode to reduce the oxidized polybenzimidazole polymer of the active layer such that an electrical current is generated; and
measuring the electrical current.

18. The method of claim 17, wherein the contacting step is conducted in the presence of an organic acid.

19. A method for detecting hydrogen peroxide, comprising:
contacting a test sample with an electrode of claim 9 such that the polybenzimidazole polymer of the active layer of the electrode is oxidized;
applying a constant voltage to the electrode to reduce the oxidized polybenzimidazole polymer of the active layer such that an electrical current is generated; and
measuring the electrical current.

20. A method of claim 19, wherein the contacting step is conducted in the presence of an organic acid.

21. An electrode for determining the $H_2O_2$ concentration in a liquid sample, the electrode comprising:
a conductor; and
an active layer formed on said conductor and including a polybenzimidazole polymer that contains at least one of the functional group of the following formula:

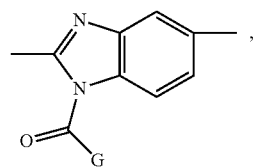
in which G is —Z—COOM, Z being a $C_2$ to $C_{22}$ divalent aliphatic group, and M being hydrogen, lithium, sodium, potassium, or ammonium.
* * * * *